United States Patent
Marsh

[11] Patent Number: 5,769,223
[45] Date of Patent: Jun. 23, 1998

[54] DEVICE FOR RECAPPING NEEDLES AND SHARPS

[75] Inventor: M. Lou Marsh, Del Mar, Calif.

[73] Assignee: Ohana Medical Concepts, LLC, Solana Beach, Calif.

[21] Appl. No.: 719,279

[22] Filed: Sep. 24, 1996

Related U.S. Application Data

[63] Continuation-in-part of Ser. No. 428,324, Apr. 25, 1995, abandoned, which is a continuation-in-part of Ser. No. 203,784, Mar. 1, 1994, abandoned.

[51] Int. Cl.⁶ ............................. B65D 85/24; A61M 5/32
[52] U.S. Cl. ........................................... 206/365; 604/192
[58] Field of Search .................................. 206/365, 366, 206/370; 604/192, 263

[56] References Cited

U.S. PATENT DOCUMENTS

| | | | |
|---|---|---|---|
| 5,078,695 | 1/1992 | Farrar, Jr. et al. | 604/192 |
| 5,172,808 | 12/1992 | Bruno | 206/366 |
| 5,209,738 | 5/1993 | Bruno | 206/366 |
| 5,311,985 | 5/1994 | Suida | 206/366 |
| 5,323,902 | 6/1994 | Palmer et al. | 206/366 |
| 5,334,151 | 8/1994 | Santilli | 206/365 |
| 5,399,169 | 3/1995 | Stein | 206/365 |
| 5,607,403 | 3/1997 | Kretzschmar et al. | 206/365 |

*Primary Examiner*—Jimmy G. Foster
*Attorney, Agent, or Firm*—Fitch, Even, Tabin & Flannery

[57] ABSTRACT

A device for holding the protective sheath of at least one hypodermic needle to permit recapping in a single-handed operation includes a hollow receptacle formed with a cavity which contains a deformable support material. The support material is penetrable by the sheath to embed the tip portion thereof in the support material and thereby hold the sheath in a substantially fixed position relative to the receptacle while the needle is withdrawn from or inserted into the sheath. The device also includes a contact adhesive on its base surface to selectively attach the device to a solid object to stabilize the receptacle during use.

20 Claims, 1 Drawing Sheet

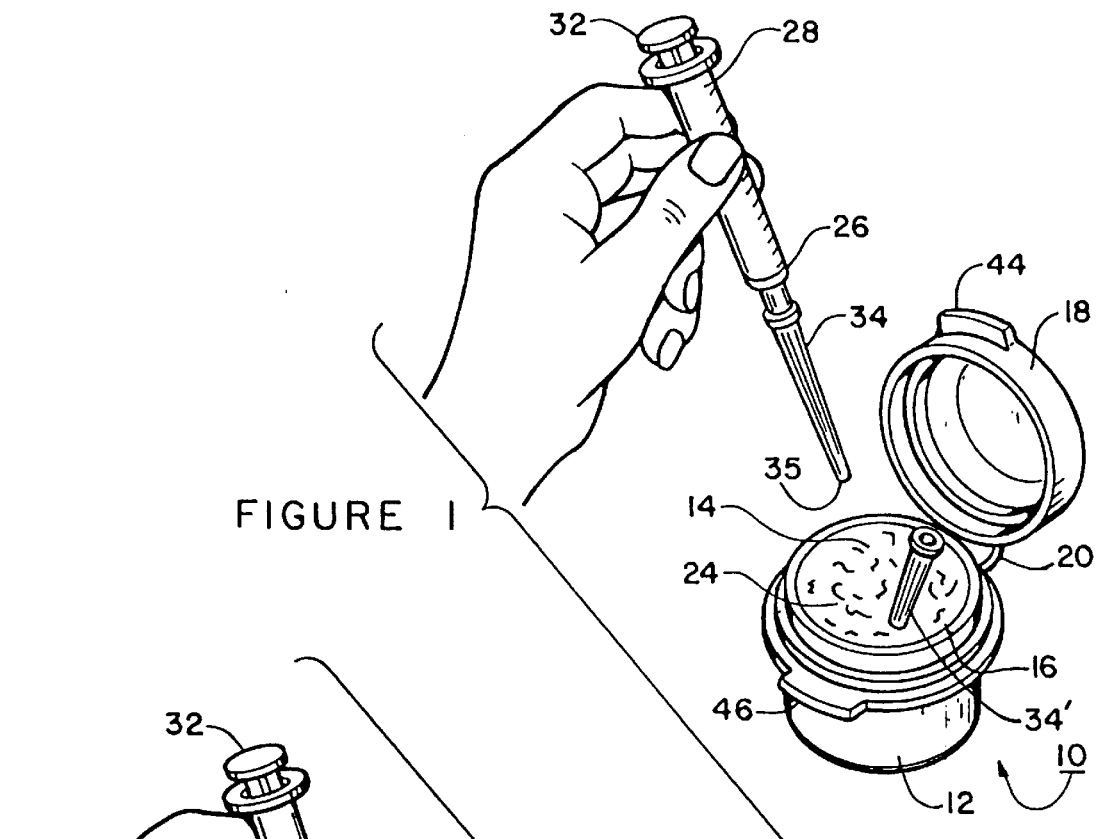
FIGURE 1
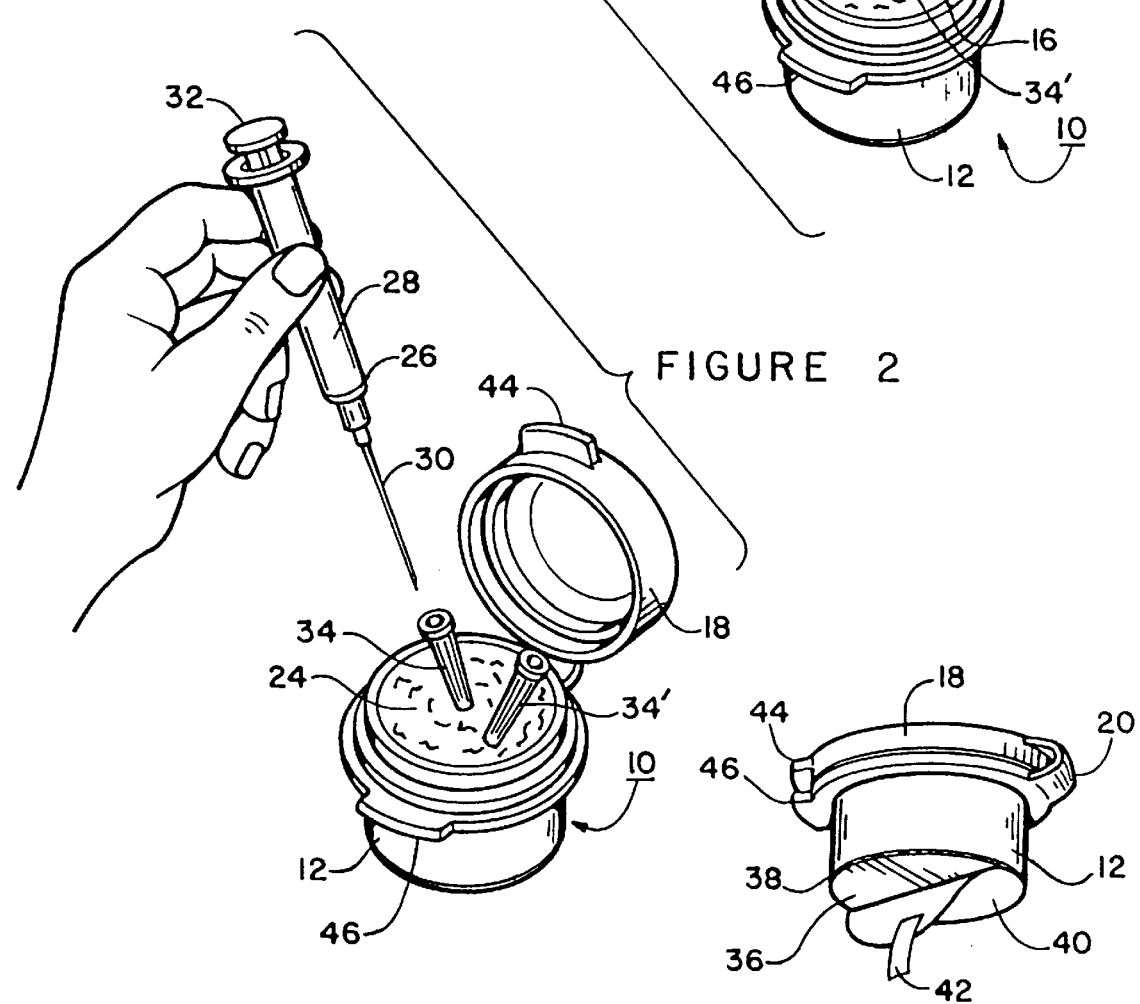
FIGURE 2
FIGURE 3

DEVICE FOR RECAPPING NEEDLES AND SHARPS

CROSS-REFERENCE TO RELATED APPLICATIONS

This is a continuation-in-part patent application of U.S. patent application Ser. No. 08/428,324, filed Apr. 25, 1995, entitled "Device for Recapping Needles and Sharps now abandoned, which is a continuation-in-part patent application of U.S. patent application Ser. No. 08/203,784, filed on Mar. 1, 1994, entitled "Device for Recapping Needles and Sharps."

FIELD OF THE INVENTION

The present invention pertains generally to medical safety devices. More particularly, the present invention pertains to a medical safety device, and its method of use, which reduces and minimizes the exposure of medical personnel to inadvertent or accidental needlesticks during the injection or withdrawal of fluids from a patient. The present invention is particularly, but not exclusively useful for recapping the needle of a hypodermic syringe in a single-handed operation.

BACKGROUND OF THE INVENTION

In any medical operation or procedure wherein a sharp pointed object such as a hypodermic needle or an intravenous catheter is to be used, there is the ever-present danger of a needlestick. This is so regardless whether the needle is being used in the active and intense environment of an operating room or in the relatively more tranquil environment of a doctor's office. Although there are many specific reasons why it is prudent to avoid a needlestick, clearly the most important reason is to avoid infections from blood borne pathogens, such as the Hepatitis and HIV viri.

Not surprisingly, several steps have been taken by governmental agencies to help protect medical personnel from inadvertent or accidental needlesticks. These steps have included the implementation of strict procedural requirements for the medical use of sharp objects (hereinafter generally referred to as "needles" or "sharps"). Further, efforts have been made to develop devices for the proper handling of needles and sharps. For example, U.S. Pat. No. 4,903,832, for an invention entitled "Method and Apparatus for Cleanly Storing and Disposing of discarded Articles" discloses a container which is used to collect and hold needles and sharps for subsequent removal from the hospital or clinic and eventual disposal. While such devices are very helpful for protecting personnel during the collection, removal and disposal of needles and sharps, they are of no use during actual use and subsequent preparation of the needle or sharp for disposal. Unfortunately, it is during these times that most needlesticks occur. Recent studies have indicated that 70% of needlesticks occur when the needle or sharp is being prepared for disposal, and only 13% occur during or after disposal.

Perhaps the most often used device which is likely to cause a needlestick is the hypodermic syringe. A hypodermic syringe typically includes a fluid chamber, a hollow needle which is in fluid communication with the fluid chamber, and a plunger which can be advanced into the chamber or withdrawn therefrom depending on whether fluid is to be injected or withdraw from the patient. For safety purposes, the needle is shrouded with a sheath or cap which surrounds the needle before it is to be used. Thus, to use a syringe, the sheath must first be removed from the needle. Then, immediately after the syringe has been used, it must be placed in a suitable container for disposal or reprocessing. Most of the time, before the needle is placed in the container for disposal, the needle is recapped by placing the sheath back over the exposed needle. As implied above, recapping the needle poses the greatest danger of an inadvertent or accidental needlestick.

One device for attempting to alleviate the inadvertent needlestick injury is disclosed in U.S. Pat. No. 5,311,985. The device disclosed therein includes a sterile block of styrofoam material, which is covered over by a protective removable plastic film. In this regard, a syringe having a sheath covering the needle portion thereof may be grasped by the user and then the sheath or cap is then inserted into the styrofoam to enable the combination of sheath and syringe to be embedded therein and supported in an upright position. The syringe can then be withdrawn from the cap, since the styrofoam block retains the sheath in place during use of the syringe.

However, it is important to be able to re-cap the syringe using a one hand operation in a convenient manner to avoid needlesticks. The patented device is not intended for the purpose of recapping the syringe, since it would be somewhat difficult to re-insert the syringe needle into the sheath and then withdraw the recapped syringe from the styrofoam block. In this regard, in actual use, it is important to be able to accomplish the replacement of the sheath in a convenient and easy manner. It is somewhat difficult to force the blunt sheath into the styrofoam to cause an opening to be formed therein by forcefully compressing the material, and then later to attempt to withdraw the embedded sheath from the styrofoam, especially with a one-hand mode of operation.

The open cell styrofoam material does not lend itself to sterilization. Thus, the patented device is not intended for use in a sterile field in an operating room.

Another problem associated with the patented device relates to the fact that the styrofoam block can become contaminated with blood during the use of the block as a holder for the sheath. The blood may seep into the open cell styrofoam and not be apparent to the user. Thus, such a situation is not desirable, and can be dangerous to the user.

In short, it would be highly desirable to have an easier to use and safer device to facilitate the replacement of the sheath onto a conventional syringe needle.

Under current regulations promulgated by the Occupational Safety and Health Administration (OSHA), 29 CFR Part 1910.1030, OSHA requires that recapping of contaminated needles and other sharps be accomplished through the use of a mechanical device or a one-handed technique. According to guidelines used in the medical community, the "One-Hand Technique" means a procedure wherein the needle of a reusable syringe is capped using only the hand holding the syringe so that the free hand is not exposed to the uncapped needle.

Understandably, recapping a hypodermic needle becomes a more difficult task, with an even greater danger of an accidental or inadvertent needlesticks, when the activity must be accomplished as a single-handed operation. There is a need, therefore, to somehow independently stabilize the protective sheath or cap of the needle while the health care provider inserts the needle into the sheath.

A recapping device which is intended to meet the requirements of the new health regulations for one hand operation is currently being marketed and appears to be disclosed in U.S. Pat. No. 4,915,698. The device includes a stand which is semi-permanently mounted on a surface and which incorporates a reusable gripper that mechanically grips needle caps. However, such a device is relatively expensive to manufacture and unduly complex.

In light of the above, it is an object of the present invention to provide a disposable recapping device and method for holding the protective sheath of at least one sharp piercing object, or a plurality of such objects, which allows re-insertion of the object relative to the sheath in a single-handed operation for recapping purposes, whereby the sheath is held so firmly in place that the object can be firmly and positively re-engaged with the sheath without a serious risk of having the sheath subsequently inadvertently fall off of the object and thus expose the user to a potentially dangerous penetration by the contaminated piercing object. Another object of the present invention is to provide a disposable recapping device and method for holding the protective sheath of a sharp piercing object which reduces the possibility of inadvertent or accidental needlesticks during re-insertion of the object into the sheath. Still another object of the present invention is to provide a disposable recapping device and method for holding the protective sheath of a sharp piercing object which is easy to use, simple to manufacture and comparatively cost effective.

SUMMARY OF THE INVENTION

One form of the invention relates to a disposable device for holding the protective sheath of a sharp piercing object, such as a hypodermic needle, for single-handed use of the object, includes a hollow container, such as a jar or cup-shaped receptacle which is formed with a cavity. The receptacle also has an opening for access into the cavity, and a lid which is hingedly attached to the lip of the receptacle at the periphery of the opening for selectively covering the opening. For the purposes of the present invention, the opening of the receptacle is sized to simultaneously receive a plurality of protective sheaths. More specifically, and for example, with a circular shaped opening the diameter of the opening will be on the order of ten to twenty times, or more, the diameter of the protective sheath. Additionally, a contact adhesive is attached to the outer base surface of the receptacle and a removable covering protects the adhesive until it is peeled away from the base surface to expose the adhesive selectively.

Deposited within the cavity of the receptacle is a deformable elastomeric support material which is penetrable by a pointed projection. An important characteristic of the deformable support material is its ability to stationarily hold the projection, once the projection has penetrated into the support material. Consequently, any unit or body attached to or held by the projection is also held in a substantially fixed position relative to the receptacle.

The device of the present invention is intended primarily, but not exclusively, for use with a hypodermic syringe which has a removable sheath that covers and protects the syringe's hypodermic needle. In the operation of the device of the present invention, the covering is removed to expose the contact adhesive on the base surface of the receptacle. The receptacle is then attached removably via the adhesive, to a supporting surface located at the immediate vicinity where the syringe is to be used, to stabilize or secure the receptacle in place on the supporting surface. Also, the lid of the device is removed from its receptacle hingedly to expose the support material in the cavity of the receptacle.

Once the device is secured in place, the sheath is engaged with the support material. Specifically, the pointed tip of the sheath is inserted into the deformable support material. The needle of the hypodermic syringe is then withdrawn from the sheath, while the sheath remains firmly embedded in the support material in a removably fixed stationary upright position. After use of the hypodermic syringe, the needle can be reinserted into the upright sheath in a single-handed manipulation. Thereafter, if desired, the recapped syringe can then be readily and conveniently withdrawn from the support material and thus can then be discarded in a conventional manner. The receptacle can then be closed by its lid or removed from the supporting surface for later use at another location.

It is to be appreciated that the device of the present invention is suitable for simultaneous use with a plurality of sharps and their respective protective sheaths. Indeed, it is a salient feature of the device of the present invention to provide a suitable support base for the protective sheaths of several hypodermic needles and other similar type medical devices having sharp protruding elements while the devices are being used.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a pictorial view of the device, which is constructed according to the present invention, and which is illustrated in the process of insertion of a capped syringe therein;

FIG. 2 is a pictorial view of the device of FIG. 1, after the protective sheath of the hypodermic needle has been removed from the syringe and is held in place therewithin to free the needle from the sheath for subsequent use; and FIG. 3 is a pictorial view of the device of FIG. 1, showing the contact adhesive on the underside of the device.

DESCRIPTION OF PREFERRED EMBODIMENTS

Referring initially to FIG. 1, the device for recapping needles and sharps is generally indicated at 10. The device 10 includes a hollow cylindrical, open top container, such as a jar or cup-shaped receptacle 12 which is formed with an internal cylindrical cavity 14 filled with a complementary shaped solid support block 24 composed of pliable deformable material for receiving and supporting syringe sheaths, such as the sheath 34 in an upright manner in preparation for the subsequent one-handed recapping operation. A circular opening 16 provides access into the cavity 14 of the receptacle 12. The device 10 also includes a lid 18 which covers over the opening 16 when the device 10 is not in use, and which is attached to the receptacle 12 by a hinge 20. For the present invention, the hinge 20 is connected to the lip 22 of the receptacle and the hinge 20 may be a structure which is integral with both the receptacle 12 and the lid 18. For an integral hinge 20 (sometimes called a "living hinge") the material which is used in the manufacture of receptacle 12, lid 18, and hinge 20 must have some degree of elasticity. Specifically, the material used should provide sufficient elasticity at the hinge 20 to allow lid 18 to be moved between the configuration shown in FIGS. 1 and 2, wherein the opening 16 is uncovered, and the configuration shown in FIG. 3, wherein the opening 16 is covered.

As seen in both FIGS. 1 and 2, the solid block 24 is penetrable by a pointed projection. Preferably, the deformable support material block 24 consists of a substance having an extremely high viscosity, such as a no post cure elastomeric silicone rubber material marketed under the trademark (NPC 40) and manufactured by Dow Corning. High viscosity for the support material block 24 is important because, though the support material block 24 must be penetrable by a pointed projection, it must also have sufficient resistance to shear or compressive forces to hold the penetrating projection in a relatively stationary upright position after penetration.

By way of example only, FIG. 1 shows the device 10 positioned for functional cooperation with a conventional hypodermic syringe 26. As perhaps best seen in FIG. 2, the hypodermic syringe 26 includes a fluid chamber 28, a hollow needle 30 which is joined in fluid communication with the fluid chamber 28, and a plunger 32 which can either be advanced into the chamber 28 to expel fluid through the needle 30, or withdrawn from the chamber 28 to draw fluid into the chamber 28. FIG. 1 also shows that a protective sheath 34 is typically used to surround and to cover the needle 30 of hypodermic syringe 26 when syringe 26 is not being operatively used.

As generally indicated in FIGS. 1 and 2, the opening 16 of receptacle 12 presents an exposed surface of the support block 24 that is relative expansive. More specifically, in comparison with a sheath 34, the diameter of the opening 16 can be ten or twenty times, or more, greater than the diameter of the sheath 34. Indeed, there is no structural limitation on the size of opening 16 and the consequently exposed surface area of the support material 24. In fact, the operational limitation on the number of sheaths 34 which can be accommodated by the device 10 is effectively determined by the number of sharps, e.g. hypodermic syringes 26, which the operator intends to use during a given procedure. Thus, the device can be used to support conveniently a plurality of sheaths simultaneously during a single procedure with a given patient (not shown). More than one needle or shape is oftentimes employed during a given procedure.

FIG. 3 shows that a contact adhesive 36, of a kind well known in the pertinent art, is deposited on the base surface 38 of receptacle 12. Further, a peel-off protective covering 40 is provided which covers the contact adhesive 36 until the adhesive 36 is to be used.

The adhesive 36 enables the device 10 to be firmly and removably attached or mounted to any conveniently located solid surface. Such an attaching surface can be firm, such as a table. The supporting surface can also be soft, such as a bed mattress or an armrest padding on an operating table. Additionally, the supporting surface can be covered by cloth or paper, and need not be horizontal. In each situation, the device can function properly for facilitating one-handed recapping procedures.

Considering now the block 24 in greater detail, the block 24 is preferably composed of an elastomeric silicone rubber material which possesses low plasticity. In this regard, the plasticity coefficient at about 25° C. should be in the range of about 55 and about 62. More particularly, the range should be between about 55.9 and about 60.6. The most preferred plasticity coefficient is about 58. In this manner, the sheath can be embedded into the block 24 and retained in its position in a generally upright manner. In this regard, as compared to other types of plastic materials, having a higher plasticity, the material would tend to relax comparatively quickly and cause the sheath to sag under the force of gravity to a position which would not be readily engageable by the syringe needle. On the other hand, the material of the block 24 is of a sufficiently low plasticity that the embedded sheath remains in a generally upright position for a sufficiently long period of time to enable the user to complete the use of one or more syringes or other such devices and then recap them, while the embedded sheaths remain in a generally upright position.

The silicone rubber material is able to sufficiently deform and receive the tip end portion of the sheath and then grip it snugly so that the sheath can remain firmly in place in an upright position. To this end, the elastomeric silicone rubber material has sufficiently small memory that it conveniently grips the sheath frictionally. Also, the substance of the block 24 can be readily re-conformed manually after each use, if desired, by applying pressure of the fingers of the user on the surface of the block 24 to smooth over the impressions left by the sheaths.

The block 24 is composed of a substance, which is stable at temperatures ranging between about −100° F. and 400° F. so that the device of the present invention can be used in different atmospheric conditions. Also, the block 24 is composed of a substance which is able to be sterilized by conventional medical techniques, such as the application of steam, heat or gas. In this manner, the substance of the block 24 is able to be readily sterilized, and thus the device 10 can be used in a sterile field in an operating room.

The substance of the block 24 is stable and is non-desiccating. In this regard, the substance of the block 24 must not be readily dehydrated and become too dry for effective use. The block 24 is composed of a material, which is translucent and colorless to permit the early detection of blood contamination which would indicate immediate disposal. In this regard, should the sheath and/or the syringe introduce blood to the block 24, the color of the blood would be immediately apparent to the user, even if the blood were to enter an opening in the block 24 and not remain at the surface.

The substance of the block 24 has a durometer hardness of about 40, and a specific gravity of about 1.10. The substance is a colorless, translucent material, and is semi-rigid.

The block 24 may also be elastomeric compounds having similar properties. For example, a material marketed by Dow Corning under the trade name NPC80, Dow Medical Grade Q7-4535, and General Electric SE6140.

It should be understood that the lid 18, when secured over the opening 16, protects the surface of the silicone rubber block 24, and also contains any bloody contamination within the container. Also, the lid 18 enhances the packaging and transportability of the unused device 10.

The material forming the block 24 must be noncorrosive, as well as the material forming the receptacle 12 (the receptacle 12 is preferably composed of a thermoplastic material). In this manner, the device 10 of the present invention can be readily sterilized for use in an operating room.

Even though the device 10 can be reused, should it become contaminated, it must be discarded in a safe manner. Thus, it is an important feature of the present invention that the device 10 is relatively inexpensive to manufacture, since it may require disposal upon contamination. The device 10 may have applications in the performance of surgical procedures, as well as other broad medical, dental and veterinary non-sterile procedures.

OPERATION

In the use and operation of the device 10 of the present invention, the user first grasps a tab or flap 42 of the covering 40 and peels off the covering 40 from the contact adhesive 36, as shown in FIG. 3. The device 10 is then secured firmly, via the contact adhesive 36, to a conveniently located solid surface, such as a table top (not shown) where the syringe 26 is to be used. This is done to stabilize or immobilize the receptacle 12 during subsequent use of the syringe. The user then grasps the tab 44 on the lid 18 and the tab 46 on the receptacle 12. By then separating the tab 44 from the tab 46, the user swings the lid 18 away from the receptacle opening 16 to expose the deformable support material block 24 in cavity 14.

By cross referencing FIGS. 1 and 2, it will be appreciated that the syringe 26 with its needle 30 initially covered by sheath 34 can be advanced toward the support material 24 in device 10 to cause the pointed sheath 34 to pass through the opening 16 to penetrate to a shallow depth into the deformable support block 24, which grips tightly the distal or closed tip end portion 35 (FIG. 1) to support firmly the sheath 34 in an upright manner as indicated in FIG. 2. In this manner, the tip portion 35 of the sheath 34 becomes firmly embedded in the block 24. Then, as indicated in FIG. 2, the syringe 26 with its needle 30 can be conveniently withdrawn from the sheath 34 for use with a patient. Thus, the user can quickly and easily uncap the syringe 26 by grasping it in one hand and plunging the tip portion 35 of the sheath to a shallow depth into the deformable block 24 to anchor the sheath within the device 10. Once so embedded, the syringe 26 can then be easily slipped out of the embedded sheath. The operation can be accomplished quickly and easily by a simple back and forth movement of the hand toward and away from the block 24 without hesitation.

As intended for the present invention, when the needle 30 is withdrawn from sheath 34, the sheath 34 remains embedded in the support block 24 in a substantially fixed orientation relative to the receptacle 12. Indeed, while the syringe 26 is being used for its intended purpose, the sheath 34 remains embedded into the support material substantially as shown in FIG. 2. As also shown in FIGS. 1 and 2, a plurality of sheaths 34 can be embedded into the support block 24. Specifically, sheath 34 and sheath 34' are shown as being exemplary of this capability.

After the intended use of the syringe 26 has been completed, the needle 30 of syringe 26 can be easily reinserted into the sheath 34 to recap the needle 30. Once the needle has been recapped with its sheath firmly engaged theron, the sheath 34 can be grasped by the user to remove the syringe and sheath 34 from the deformable support block 24. The recapped syringe 26 can then be discarded or reprocessed, as desired. Importantly, and as can be easily appreciated, the entire recapping operation can be accomplished using only one hand.

While the particular Device for Recapping Needles and Sharps as herein shown and disclosed in detail is fully capable of obtaining the objects and providing the advantages herein before stated, it is to be understood that it is merely illustrative of the presently preferred embodiments of the invention and that no limitations are intended to the details of construction or designed herein shown other than as described in the appended claims.

I claim:

1. A device for removing and holding protective sheaths of sharp piercing objects during single-handed use of the object, comprising:

a hollow container having a cavity therein, said container having an opening into said cavity, said opening being sized to simultaneously receive a plurality of the sheaths therethrough;

a solid support block, said support block being composed of a deformable semi-rigid elastomeric material for receiving and gripping the sheaths and being disposed within said cavity to present an exposed surface thereof at said opening, said exposed surface of said support material being penetrable by said sheaths to surround and embed tip portions of the sheaths therein to grip the sheaths in substantially fixed upright positions relative to said container while the objects are withdrawn from or inserted into the sheath; and said support block material having low memory and having low plasticity coefficient sufficient to grip firmly and to retain the embedded sheaths in their upright positions for a sufficiently long period of time to permit the user to employ the objects before re-inserting the objects back into their respective sheaths, said material being able to withstand relatively high temperatures to enable the device to be sterilized, said material being generally translucent to enable the user to readily determine contamination thereof.

2. A device as recited in claim 1, wherein said support block material is an uncured elastomeric silicone rubber material.

3. A device as recited in claim 2, wherein said support block material has a plasticity coefficient of between about 55.9 and about 60.6 at about 25° C.

4. A device as recited in claim 3, wherein said plasticity coefficient is about 58 at about 25° C.

5. A device as recited in claim 4, wherein said material has a durometer hardness of about 40, and a specific gravity of about 1.10.

6. A device as recited in claim 2, wherein said material is stable in form between about minus 100 degrees Fahrenheit and about 400 degrees Fahrenheit.

7. A device as recited in claim 1 further comprising a contact adhesive attached to said base for stabilizing said device.

8. A device as recited in claim 1 further comprising a lid, said lid being hingedly attached to said receptacle for selectively covering said opening.

9. A device as recited in claim 1 wherein said support material is an elastomeric silicone rubber.

10. A device as recited in claim 1 wherein said object is a hypodermic needle.

11. A device for removing and holding a protective sheath of a sharp piercing object during single-handed use of the object, which comprises:

a deformable elastomeric support material having a plasticity coefficient between about 55.9 and about 60.6 at about 20° C.;

means for containing the deformable elastomeric support material, said containing means having an opening to expose said support material and said opening being sized to simultaneously receive a plurality of said sheaths therethrough;

means attached to said containing means for selectively exposing a portion of said support material at said opening of said containing means to allow penetration of said support material by at least one said sheath to embed said sheath therein and to hold said sheath in a substantially fixed relationship with said containing means while said object is withdrawn from or inserted into said sheath; and means attached to said containing means for stabilizing said containing means.

12. A device as recited in claim 11 wherein said containing means is a hollow receptacle formed with a cavity for receiving said support material therein, said receptacle having a base.

13. A device as recited in claim 12 wherein said stabilizing means is a contact adhesive attached to said base for stabilizing said device.

14. A device as recited in claim 13 wherein said exposing means is a lid, said lid being hingedly attached to said receptacle for selectively covering said opening.

15. A device as recited in claim 14 wherein said support material is an elastomeric silicone rubber.

16. A device as recited in claim 15 wherein said object is a hypodermic needle.

17. A method for protecting a user from accidental needle sticks during single-handed operation of a hypodermic needle having a removable protective sheath, which comprises the steps of:

containing a deformable elastomeric support material in a cavity of a hollow receptacle, said receptacle having an opening sized to simultaneously receive a plurality of said sheaths therethrough, said deformable elastomeric support material having a low plasticity coefficient between about 55.9 and about 60.6 at about 25° C.;

stabilizing the hollow receptacle;

penetrating said support material at said opening with at least one said protective sheath to embed said sheath in said support material and hold said sheath therein in a substantially fixed position relative to said receptacle;

withdrawing said hypodermic needle from said protective sheath while said sheath remains engaged with said support material; and inserting said hypodermic needle into said protective sheath to recap said needle while said sheath remains engaged with said support material.

18. A method as recited in claim 17 wherein said stabilizing step is accomplished by:

exposing an adhesive on a base of said receptacle; and affixing said receptacle to a conveniently located solid surface via said adhesive.

19. A method as recited in claim 17 further comprising the step of removing said recapped needle, with said sheath, from said support material.

20. A method as recited in claim 17 wherein a plurality of protective sheaths penetrate said support material.

* * * * *